(12) United States Patent
Morero

(10) Patent No.: US 8,998,946 B2
(45) Date of Patent: Apr. 7, 2015

(54) BLOOD CLOT REMOVAL DEVICE

(75) Inventor: Massimo Morero, Roncadelle (IT)

(73) Assignee: Invatec S.p.a., Roncadelle (BS) (IT)

(*) Notice: Subject to any disclaimer, the term of this patent is extended or adjusted under 35 U.S.C. 154(b) by 448 days.

(21) Appl. No.: 13/140,403

(22) PCT Filed: Dec. 30, 2008

(86) PCT No.: PCT/IT2008/000806
§ 371 (c)(1),
(2), (4) Date: Aug. 10, 2011

(87) PCT Pub. No.: WO2006/084019
PCT Pub. Date: Aug. 10, 2006

(65) Prior Publication Data
US 2011/0295305 A1  Dec. 1, 2011

(51) Int. Cl.
*A61M 29/00* (2006.01)
*A61B 17/221* (2006.01)
*A61B 17/00* (2006.01)
*A61B 17/22* (2006.01)

(52) U.S. Cl.
CPC ..... *A61B 17/221* (2013.01); *A61B 2017/00867* (2013.01); *A61B 2017/22034* (2013.01); *A61B 2017/2217* (2013.01)

(58) Field of Classification Search
USPC .................. 606/113, 127, 159, 200; 604/508
See application file for complete search history.

(56) References Cited

U.S. PATENT DOCUMENTS

| 4,706,671 | A | 11/1987 | Weinrib |
| 5,554,114 | A * | 9/1996 | Wallace et al. ............... 604/508 |
| 2002/0072764 | A1 * | 6/2002 | Sepetka et al. ............... 606/200 |
| 2003/0040762 | A1 * | 2/2003 | Dorros et al. ............... 606/159 |
| 2004/0030375 | A1 * | 2/2004 | Pierce ........................... 607/125 |
| 2006/0009784 | A1 | 1/2006 | Behl et al. |

FOREIGN PATENT DOCUMENTS

| EP | 0 330 843 | 9/1989 |
| WO | WO 2006/084019 | 8/2006 |

* cited by examiner

*Primary Examiner* — Thomas McEvoy

(57) ABSTRACT

A blood clot removal device (1), comprising a capture member (2) having a tubular body (3) of prevailing longitudinal extension and provided with a lumen (10) extending longitudinally in said tubular body (3), at least one proximal portion (4), at least one distal portion (5), an apical end (6) of said distal portion (5), and a tip (7); said at least one distal portion (5) of said capture member (2) having at least one helical length (8) provided, with coils (16) wrapped in a helical manner forming a pitch (p) therebetween in the longitudinal direction and adapted to the capture of blood clots (9); an inner cable (11) received in said longitudinal lumen (10) of said tubular body (3) so as to remain within said tubular body (3) helical length (8), said inner cable (11) comprising a proximal length (12) having a proximal maneuvering end (13) and a distal length (14) provided with a tip (15); wherein said tip (15) of said inner cable (11) is secured to said apical end (6) of said capture member (2) tubular body (3), said tip (15) being firmly secured to said apical end (6) so that, when said inner cable (11) is subjected to a relative movement relative to the capture member (2) in the proximal direction, said inner cable (11) brings the tubular body (3) apical end (6) closer to the proximal portion thereof, shortening the pitch (p) of said coils (16) of the helical length (8) of the blood clot (9) capture member (2).

30 Claims, 14 Drawing Sheets

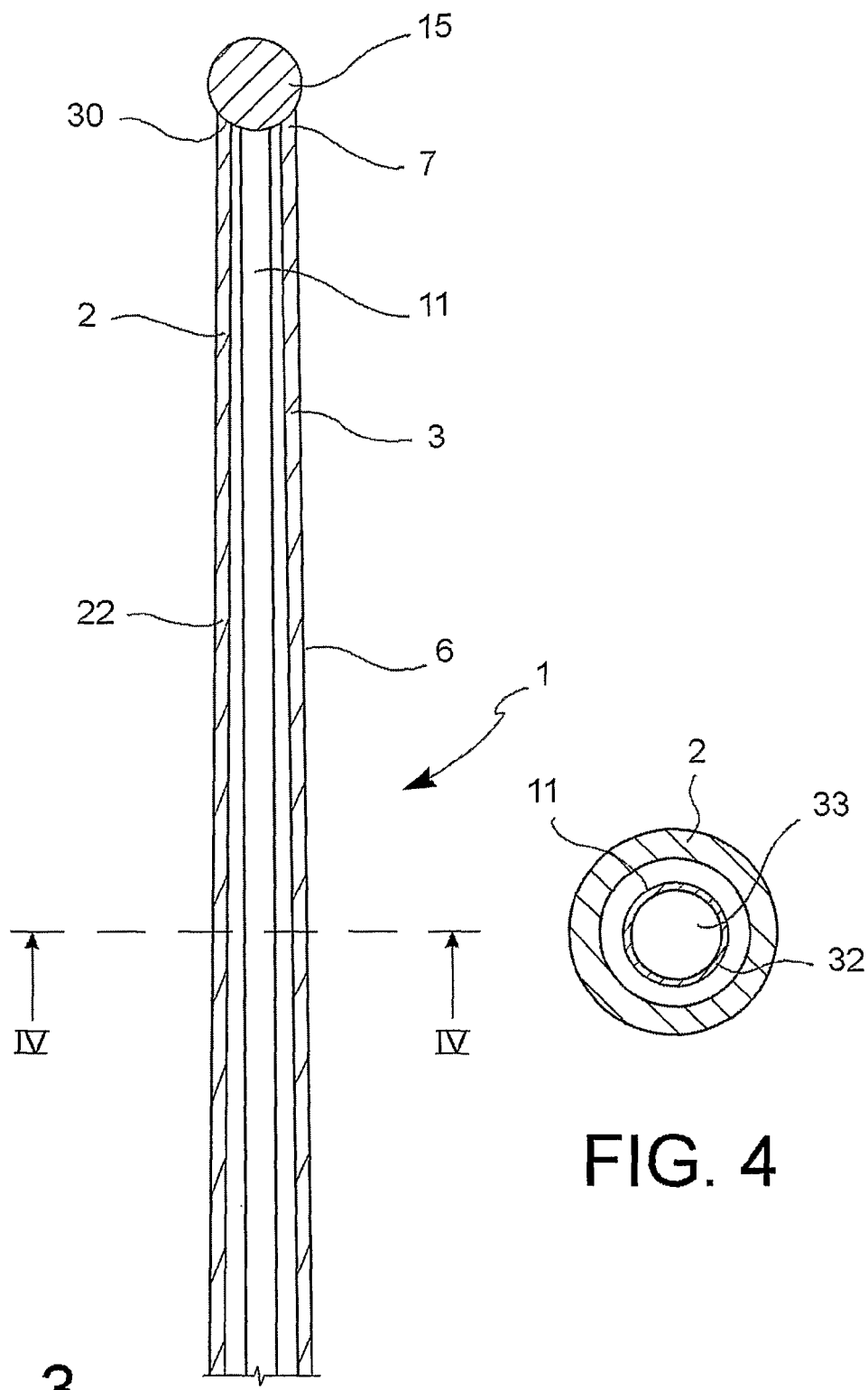

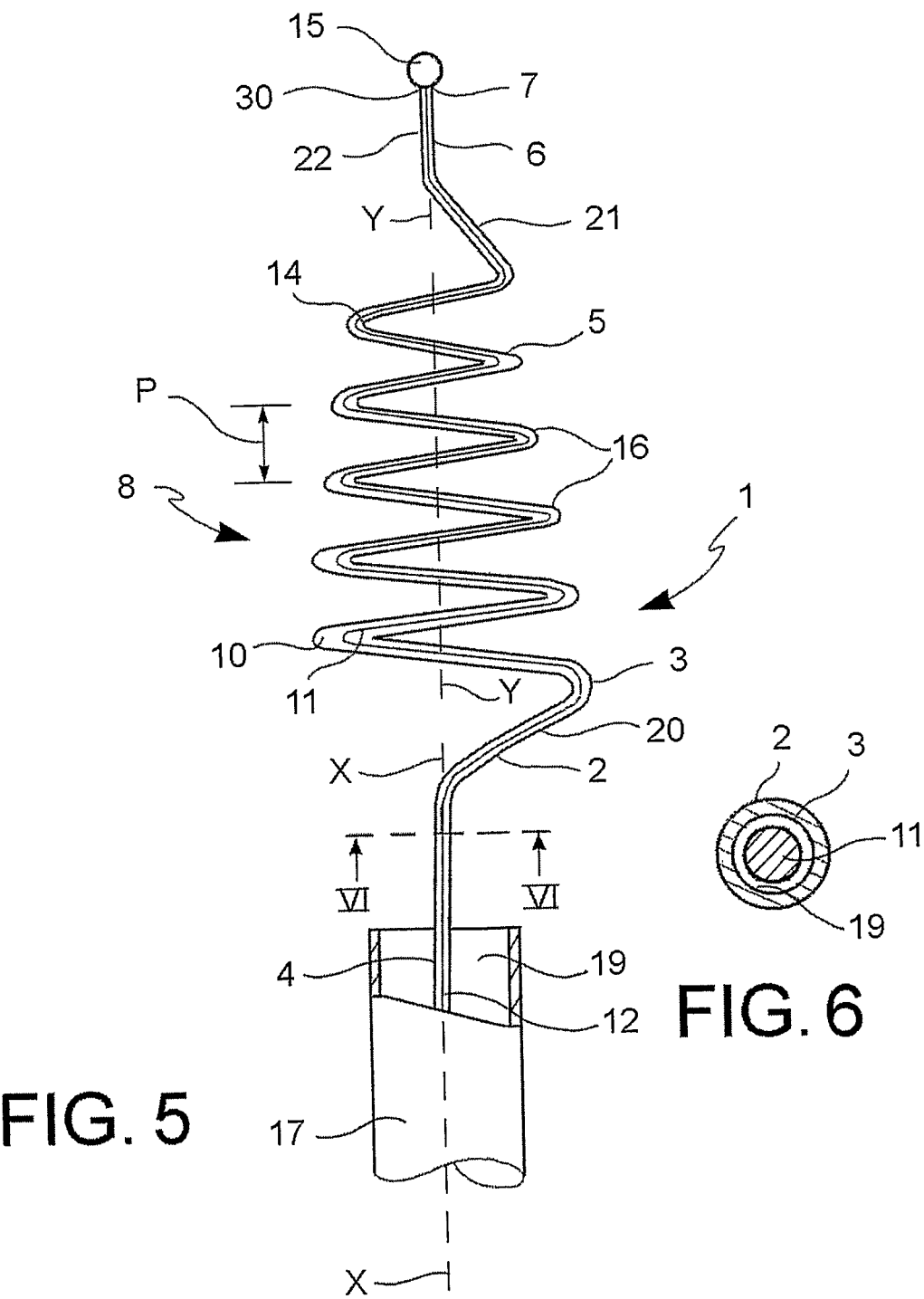

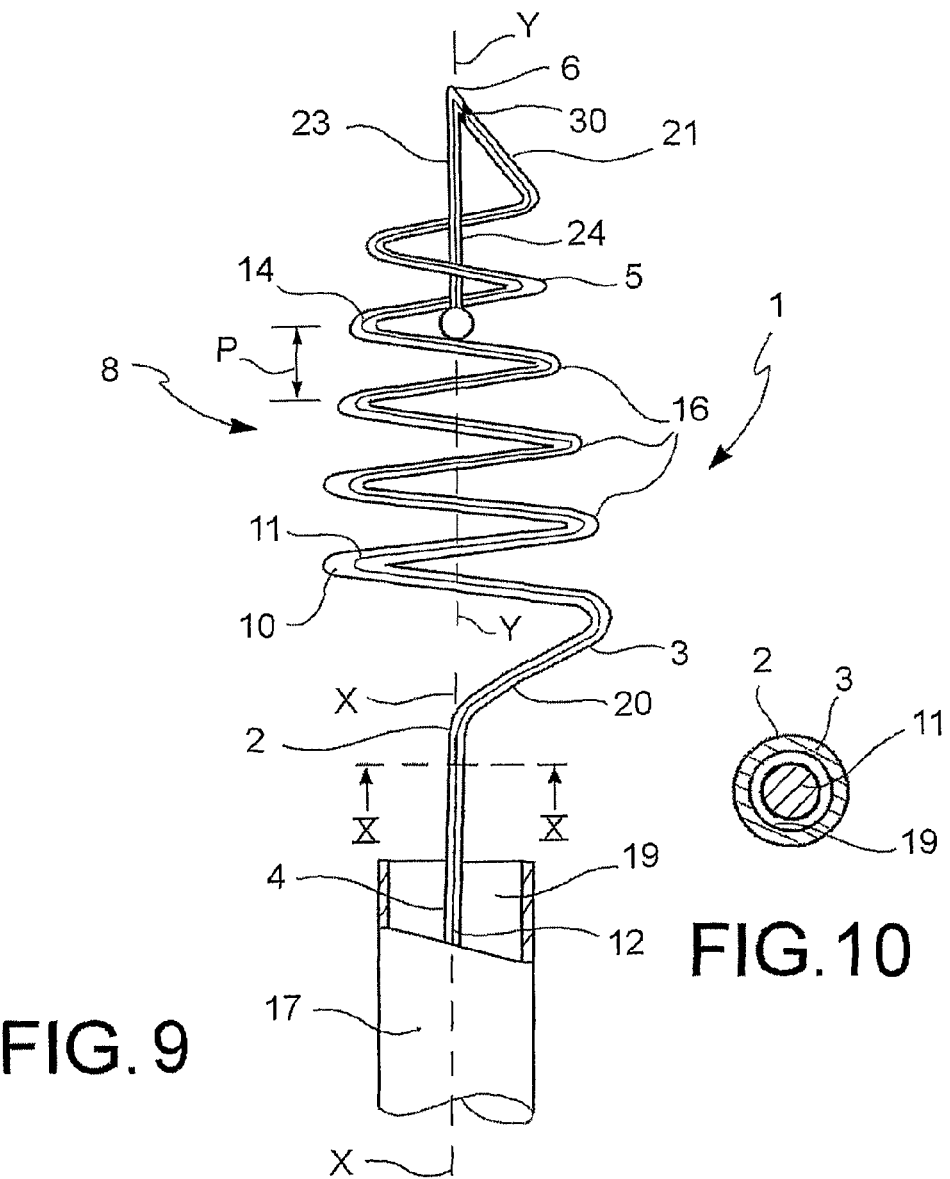

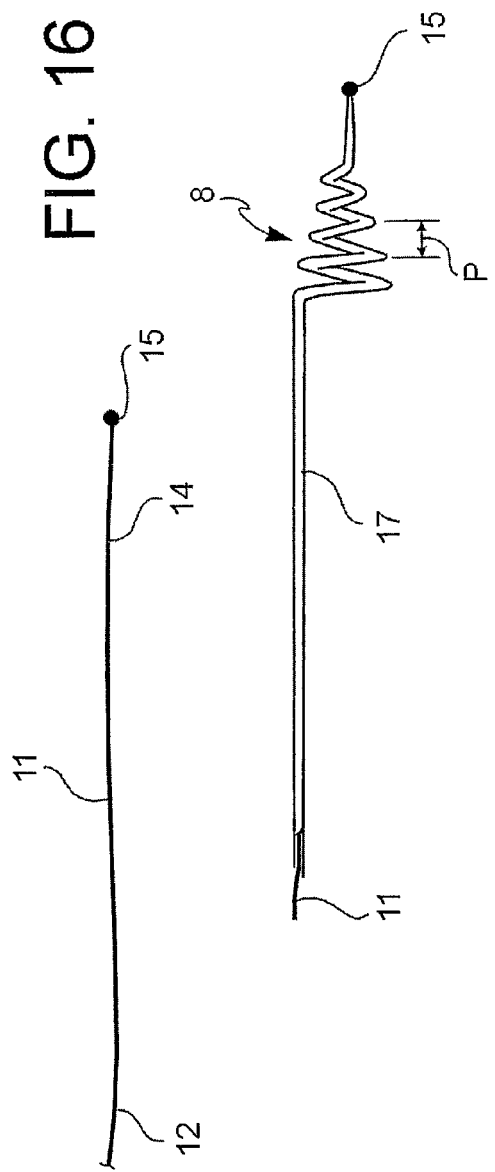

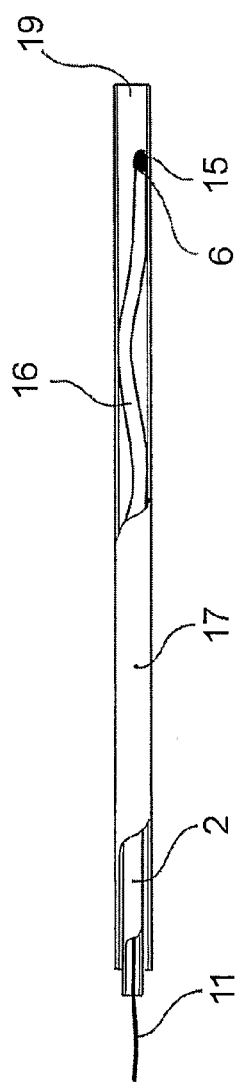
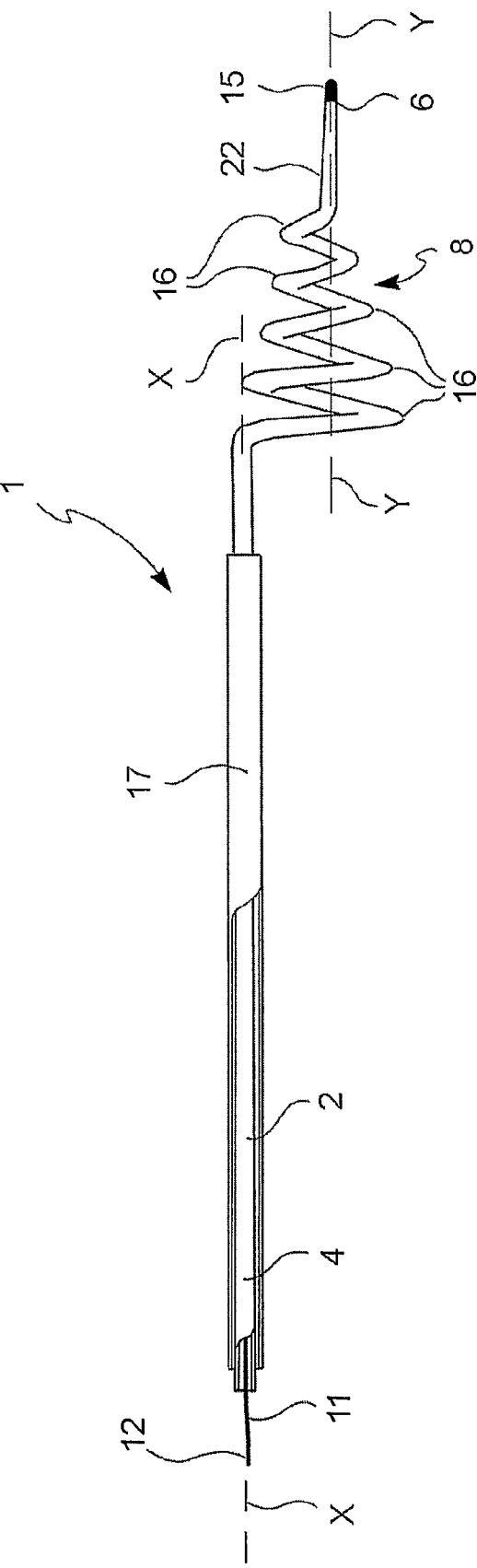

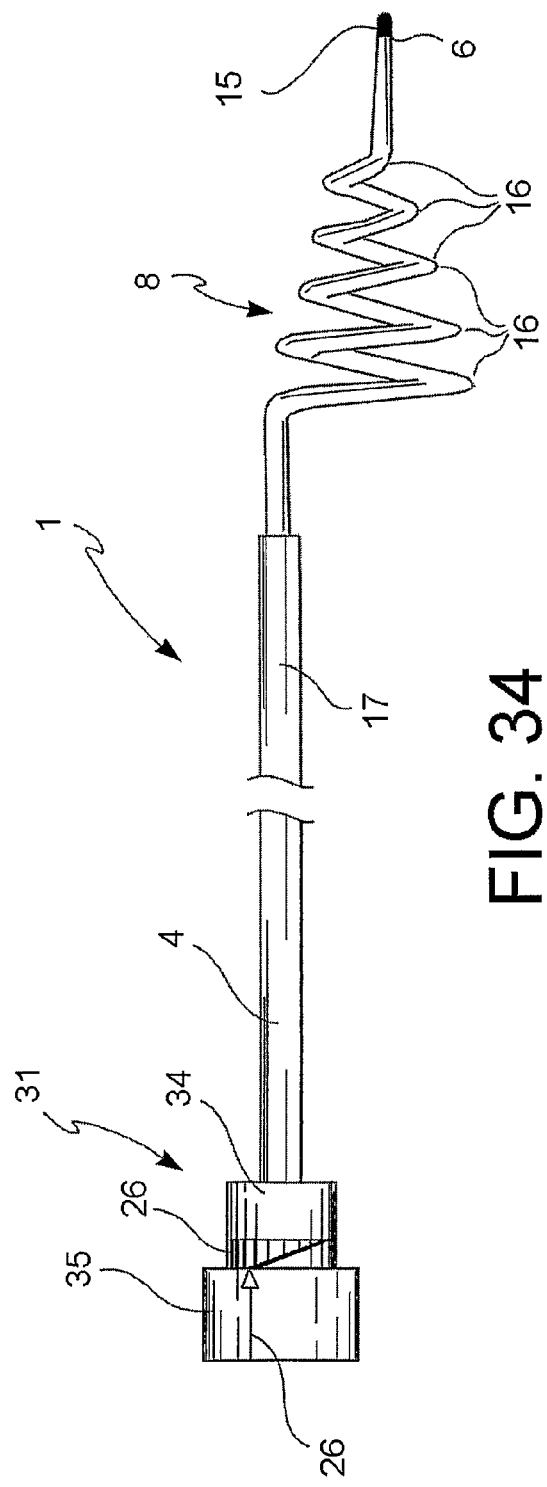
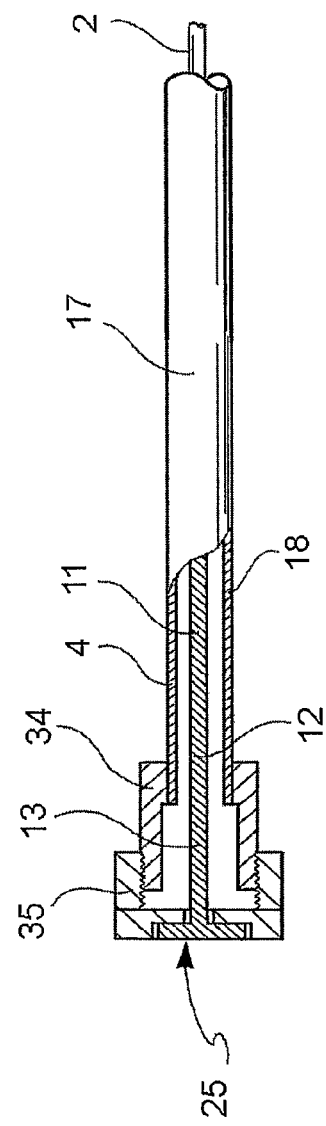
FIG. 34
FIG. 35

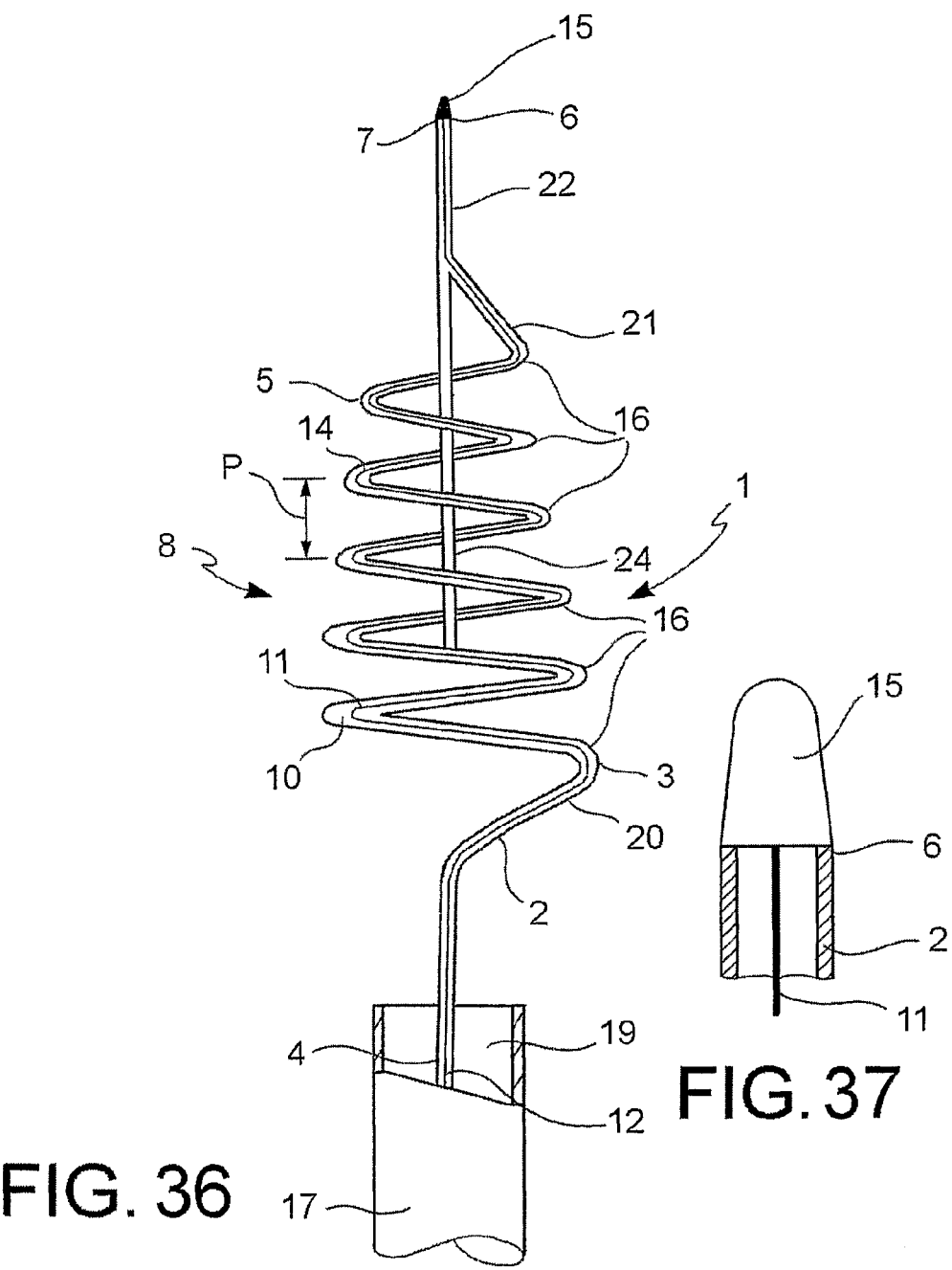

BLOOD CLOT REMOVAL DEVICE

FIELD OF THE INVENTION

The present invention relates to a blood clot removal device.

Particularly, the present invention relates to an apparatus comprising a device for the removal of emboli or blood clots, for example, blood material, as well as to the removal of calculi or similar obstructions of anatomical ducts or vessels. Therefore, herein below by "blood clots" is meant any objects which even only partially obstruct a duct or vessel and which have to be removed in order to restore the recanalization or patency of the duct or vessel.

STATE OF THE ART DESCRIPTION

Blood clot removal devices are known, which allow removing organic material from within anatomical lumens.

These known devices comprise a catheter and an inner member with a longitudinal proximal portion and a helical distal portion. This distal part is in elastic material which is able, when urged, to pass from the helical configuration to a rectilinear one.

Two different modes of deploying and using blood clot removal devices are known from the prior art.

In accordance with some known solutions, the physician introduces the blood clot removal device in the anatomical lumen with the helical distal part retracted in the linear configuration within a catheter. Once the blood clot has been reached, the physician passes beyond it with the catheter, so as to bring the distal part of the latter beyond the blood clot, then withdrawing the device, deploying the helical distal part thereof, and finally returning the device, thus capturing the blood clot.

In accordance with other known solutions, the device provided with a helical distal portion has an inner lumen which receives a wire. When the wire is urged into the device, the helical distal portion "unwraps", urging itself in a linear position, thus allowing the device to be introduced within anatomical vessels. Once the blood clot has been passed beyond, the cable is released and withdrawn, allowing to the device elastic distal portion, which is no more stressed, to return to a helical configuration.

With the helical distal portion deployed, the device is retracted, thus capturing the blood clot. In this pulling step of the device, the blood clot exerts a resistance forcing against the vessel walls, urging the device and particularly the helical distal portion thereof. This helical portion, due to the pulling stress and the resistance to the progression of the blood clot, warps, thus stretching the coils thereof to the extent that in some cases a dangerous breakage of the blood clot mass is reached.

From U.S. Pat. No. 4,706,671, a system for removing blood clots is known, having a helical section which grasps the clot of the thrombus. Particularly, this known solution discloses a tubular catheter in elastomeric silicone material, known as SILASTIC™, in which a freely withdrawable wire is introduced. This wire is pushed into the catheter by urging the catheter and stretching it to extend the helical section thereof, with the aim of introducing it into the vessel to be treated. Once the system has been positioned, the wire is completely withdrawn from the catheter to bring the section thereof back to the helical position, then inserting into the catheter lumen, which otherwise would result to be too much deformable, a pressurized fluid which stiffens the body thereof during the blood clot gripping maneuvers. Externally to the catheter a second wire is present, which is connected to the tip thereof, and able to strain the helical section thereof.

From WO 02/28291, a tool for removing blood clots is known, having a metal cannula with a flexible distal section in which a wire is received which is proximally secured to an actuator which exerts a traction action thereof. Distally, the wire is anchored to the flexible distal section, and transmits to the latter the action of the actuator. The flexible section is manufactured so as to move to a rectilinear position when compressed by the wire distally anchored thereto, and to a helical position when released. Therefore, when the actuator exerts a traction action on the wire, this urges the flexible section and brings it to a rectilinear configuration, while when the actuator releases the wire, the released flexible section moves to a helical configuration.

This known solution, while being advantageous under many points of view, is unsuitable to procedures in small-sized blood vessels. In fact, the flexible section of the cannula, in order to be able to be brought to a rectilinear position, is manufactured via a helically wrapped wire-shaped member which, when compressed by the action of the actuator, packs its coils, thus taking an overall rectilinear arrangement. The body of the coiled cannula, in order to be able to oppose the capture and return action of the blood clot, results to be of considerable transversal dimensions and unsuitable to smaller, specially cerebral, vessels, where in most cases the need to remove the blood clots is more felt.

From U.S. Pat. No. 4,762,130, a catheter for removing blood clots is known, having a helical balloon which, when deployed, grasps the blood clot mass to be removed. In a second embodiment, there is provided a balloon catheter enveloping a catheter body. A helical wire is introduced into the balloon, which, when contracted, expands the coils thereof, thus shaping the balloon in a helical configuration, so as to entrap a blood clot mass.

Also in this case, the transversal dimension of the balloon catheter results to be particularly invasive and unsuitable to the use in small-sized vessels.

TECHNICAL PROBLEM

The problem underlying the present invention is to overcome the drawbacks of the art hereto known by providing a blood clot removal device and a method for implementing such device, capable of an efficient removal of the blood clots also from vessels of reduced transversal dimensions.

Particularly, a problem of the present invention is to remove emboli from small cerebral vessels while avoiding that, during the removal, an undue strain of the device results in the separation of portions of the mass to be removed, which portions, when released from the rest of the mass, can escape the capture and travel the vessel, thus obstructing it in lengths of still more reduced dimensions.

A further task of the present invention is also a method for assembling a blood clot removal device and a deployment and capture method which ensures a precise positioning of the device and a most complete removal possible of the blood clot also from vessels of small transversal dimensions.

SUMMARY OF THE INVENTION

These and other objects are achieved by a device according to claim 1, a device assembling method according to claim 22, and a method according to claim 27.

In accordance with an embodiment of the present invention, a blood clot removal device comprises a capture member having a tubular body of prevailing longitudinal extension, and provided with a lumen extending longitudinally in said tubular body. Said tubular body has at least one proximal portion, at least one distal portion, an apical end of said distal portion, and a tip.

Said at least one distal portion of said capture member has at least one helical length provided with coils wrapped in an helical manner, forming a pitch therebetween in the longitudinal direction, and arranged one relative to the other so as to be adapted to the capture of blood clots.

Said longitudinal lumen of said tubular body receives an inner cable so that it remains within said helical length. Said inner cable comprises a proximal length having a proximal maneuvering end, and a distal length provided with a tip.

In accordance with an embodiment, but not necessarily, said maneuvering end of the cable is adapted to proximally protrude from said capture member.

Advantageously, at least one securing portion of said distal length of said inner cable is secured to said apical end of said capture member tubular body. Said securing portion is preferably firmly secured to said apical end so that, when said inner cable is subjected to a relative movement relative to the capture member in the proximal direction, said inner cable approaches the apical end of the tubular body to the proximal portion thereof shortening the pitch of said coils of the helical length.

With particular advantage, the movement in the proximal direction of the inner cable brings the capture member from a more extended status to a shortened status.

Preferably, during the traction of the cable, it is avoided that the coils of the helical length can contact one another or be packed, avoiding compressing the blood clot mass and disaggregating it into fragments.

With particular advantage, in accordance with a particular embodiment, the device comprises a micro-catheter in which the capture member of the blood clot is slidably introduced. This capture member has an inner lumen, an essentially straight proximal portion, and a helical flexible distal portion. Furthermore, a metal cable is provided, which is received in the capture member lumen and anchored to the distal end thereof.

In use, when the micro-catheter distal end is arranged beyond the blood clot, the physician deploys the capture member, releasing it from the micro-catheter inner lumen. The flexible distal portion of the capture member protruding from the micro-catheter locates itself according to the helical configuration thereof, and entraps the blood clot.

When the physician pulls or retracts the capture member backwards or proximally, in order to remove the blood clot from the vessel, a stressed status results, which may become excessive on the helical portion, resulting in an increase the helical pitch.

This situations results to be apparent to the physician during the procedure, for example, by monitoring the operative area with a continuous angiography, radiography, or radioscopy, and noticing the strain of the helical portion, which is more radio-opaque than the surrounding tissues, which exhibits a mutual spacing apart of the coils.

When this situation occurs, the physician discontinues the traction he is exerting to withdraw the capture member with the anchored blood clot, and pulls, directly or by maneuvering means, only the inner cable, while keeping the capture member steady. In this manner, the cable being constrained with the distal length thereof to the capture member apical end, the capture member distal part is pulled, thus bringing it closer to the proximal portion thereof. In this manner, the capture member helical length returns from the extended position to the shortened configuration thereof of the helical length coils, therefore allowing the physician to resume the traction of the capture member to withdraw the blood clot from the vessel. This inner cable traction action, which brings the anchoring member distal end closer, also allows a stiffening of the device by preloading it.

In the case where, during the blood clot withdrawal operation, an undue strain of the helical length should occur, the physician will be able to repeat the above-described operation.

Thanks to the fact that only one cable arranged internally to the same capture member is provided associated to the capture member, the device results to be particularly not very cumbersome, with a very reduced progression profile, therefore it can be also used in vessels with reduced or very reduced section.

Thanks to the fact that the device, in order to be introduced in the branch where the blood clot is present, in accordance with an embodiment, does not require to be stiffened in a stretched position or with the coils strained or extended to bring the distal portion in an essentially rectilinear configuration, in other words, it does not need a wire which, once internally pushed in the distal direction, extends the distal portion in the rectilinear position, thus stiffening the device, it is possible to keep an optimal maneuverability which ensures a higher progression easiness along the optional tortuous paths of the vessels to reach the vessel length to be treated. Therefore, the proposed solution has a capture member which is particularly flexible and with optimal traceability performance.

With still further advantage, thanks to the provision at least of the helical length in elastic material, for example, preferably a shape memory material, for example, in Nitinol™, it is possible to capture and retain the blood clot during the withdrawal, but at the same time it is possible to keep a sufficient flexibility of the device to easily navigate in the tortuousness of the vessel branches, for example, the blood vessels, and at the same time to have a sufficiently robust device to withdraw the blood clot from the vessel, while avoiding undue strains or breakages.

BRIEF DESCRIPTION OF THE DRAWINGS

The technical characteristics of the invention, according to the above-mentioned objects, are traceable from the contents of the claims, and the advantages thereof will result to be more clearly understood in the following detailed description, given with reference to the annexed drawings, which represent merely exemplary and non-limiting embodiments thereof, in which:

FIG. 3 illustrates in sectional side view the distal end of a capture member with inner cable according to a different embodiment;

FIG. 4 illustrates a sectional view of the capture member of FIG. 3 according to the line IV-IV;

FIG. 5 shows, according to a further embodiment, a sectional view of a micro-catheter distal end from which a capture member distally protrudes in a deployed and relaxed position, in which an inner cable is received;

FIG. 6 shows the section according to the line VI-VI of the capture member with cable of FIG. 5;

FIG. 9 shows, according to a still further embodiment, a sectional view of a micro-catheter distal end from which a capture member distally protrudes in a deployed and relaxed position, in which an inner cable is received;

FIG. 10 shows the section according to the line X-X of the capture member with cable of FIG. 9;

FIG. 16 illustrates a side view of the distal part of an inner cable;

FIG. 17 shows a side view of the distal part of a capture member;

FIG. 18 shows a side view of the distal part of a micro-catheter;

FIG. 19 illustrates a partially sectional side view of the distal part of a capture member in which an inner cable is received;

FIG. 20 illustrates a partially sectional side view of a micro-catheter distal part in which a capture member is wholly received with inner cable in an essentially rectilinear position;

FIG. 21 shows a partially sectional side view of a micro-catheter distal part from which the helical length of a capture member with inner cable according to a further embodiment completely protrudes, in which the capture member proximal part is asymmetrically arranged relative to the longitudinal axis around which helical length deploys;

FIG. 34 illustrates a partially sectional side view of an embodiment of a capture member with inner cable and maneuvering members of the cable;

FIG. 35 shows a partially sectional side view of the proximal part of the device according to the FIG. 34;

FIG. 36 illustrates, according to a still further embodiment, a sectional view of a micro-catheter distal end from which a capture member distally protrudes in a deployed and relaxed position, in which an inner cable is received; and FIG. 37 illustrates, according to a still further embodiment, in a sectional side view, a capture member distal end with inner cable according to a different embodiment.

Figures 1, 2:
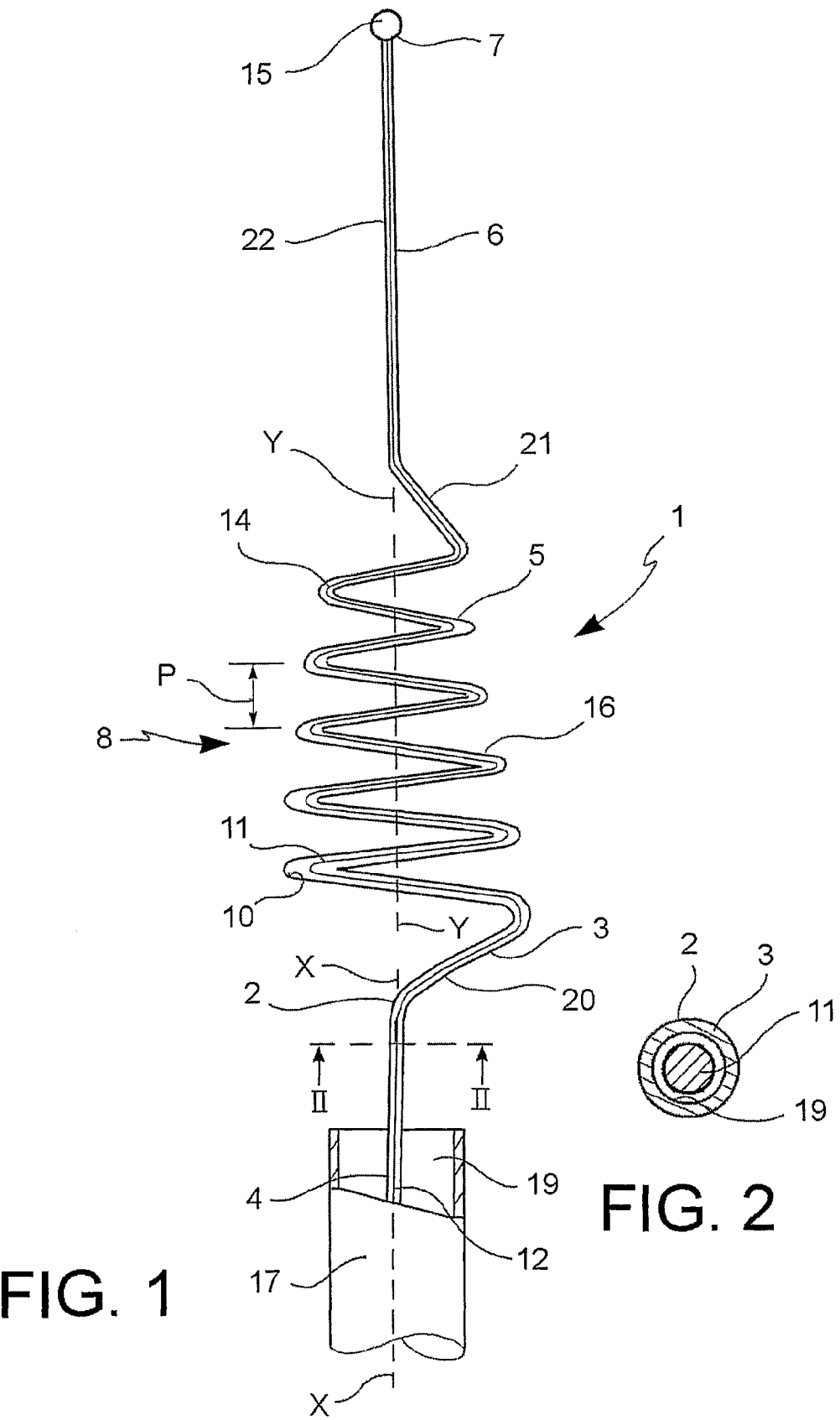
FIG. 1 shows a partially sectional side view of a micro-catheter distal length from which a capture member in deployed and relaxed position distally protrudes, in which an inner cable is received.
FIG. 2 shows the cross-section of the capture member according to the line II-II of FIG. 1.

DETAILED DESCRIPTION OF SOME
PREFERRED EMBODIMENTS OF THE
INVENTION

In accordance with a general embodiment, a blood clot removal device 1 comprises a capture member 2 having tubular body 3 with prevailing longitudinal extension. Said tubular body 3 comprises a lumen 10 longitudinally extending in said body 3 from a proximal end thereof to a distal end thereof. Said tubular body 3 comprises at least one proximal portion 4, at least one distal portion 5, an apical end 6 of said distal portion 5, and a tip 7 (FIGS. 1, 5, 7, 9, 21, 34, and 36).

Advantageously, said at least one distal portion 5 of said capture member comprises at least one helical length 8 provided with coils 16. These coils 16 are wrapped in a helical manner and form one to the other a pitch "p" in the longitudinal direction which, in accordance with an embodiment, is constant when the helical length 8 is relaxed or in non-stressed conditions.

Said coils 16 of said helical length 8 are suitably arranged, when deployed in non-stressed conditions, to the capture of blood clots 9 present in a vessel having transversal dimensions, for example, essentially slightly above the helical length maximum transversal dimension.

Advantageously, an inner cable 11 is received in said longitudinal lumen 10 of said tubular body 3.

In accordance with an embodiment, said inner cable 11 remains inside the tubular body 3 also along said helical length 8.

In accordance with an embodiment, said inner cable 11 comprises a proximal length 12, comprising a proximal maneuvering end 13, and a distal length 14, provided with a tip 15.

In accordance with an embodiment, not necessarily present in the other embodiments, said proximal maneuvering end 13 is adapted to proximally protrude from said capture member 2.

Advantageously, at least one securing portion 30 of said distal length 14 of said inner cable 11 is secured to said apical end 6 of said tubular body 3 of the capture member 2. With further advantage, said securing portion 30 is firmly secured to said apical end 6 so that, when said inner cable 11 is subjected to a relative movement relative to the capture member 2 in the proximal direction, said inner cable 11 brings the apical end 6 of the tubular body 3 closer to the proximal portion thereof 4, shortening the pitch "p" of said coils 16 of the capture member 2 helical length 8.

Preferably, the movement to the proximal direction of the inner cable 11 brings the capture member 2 from a more tensioned or extended status to a less tensioned or shortened status, preferably avoiding bringing the coils 16 mutually in contact or packed.

In accordance with an embodiment, said securing portion 30 of said inner cable 11 is the cable 11 tip 15, and said tubular body 3 apical end 6 is the tubular body 3 tip 7.

In accordance with an embodiment, said capture member 2, at least in the helical length 8, is in a shape memory elastic material, for example, superelastic, preferably in Nitinol™, for example, adapted to remain elastic also when stressed in an essentially rectilinear deployed configuration.

In accordance with an embodiment, at least one proximal length 4 of the capture member 2 is in a first material adapted to support at least the stresses adapted to retract said capture member 2 to remove a blood clot, and at least one helical length 8 of the capture member 2 in a shape memory elastic material, for example, adapted to remain elastic also when stressed in an essentially rectilinear deployed configuration.

In accordance with an embodiment, said helical length 8 extends along a longitudinal axis Y-Y from a proximal end 20 to a distal end 21, and comprises a plurality of coils 16 which little by little approach said longitudinal axis Y-Y passing from said proximal end 20 to said distal end 21, so as to constitute a receptacle or pocket arranged transversally to a vessel and to form a seat able to capture, at least partially contain, and retain, a blood clot to be removed.

In accordance with an embodiment, said helical length 8 has a dimension with a conical or frusto-conical shape, but advantageously, in accordance with a further embodiment, said helical length 8 has a dimension with a spherical cap shape.

In accordance with an embodiment, said coils 16 of said helical length 8 essentially have a helical shape, for example, but not necessarily, cylindrical, and advantageously, in accordance with a further embodiment, with a diameter decreasing from 5 mm at the proximal end 20 of the helical length 8 to a diameter of 1 mm at the distal end 21 of the helical length 8.

In accordance with an embodiment, said helical length 8 has from 3 (three) to 9 (nine) coils, preferably it has 6 (six) coils.

In accordance with an embodiment, the coils 16 of said helical length 8 are arranged eccentrically relative to the proximal portion 4 of the tubular body 3 of the capture member 2 so as to let said helical length 8 free to perform its capturing action on a blood clot 9 (FIGS. 17, 19, 21, and 34).

However, in accordance with an embodiment, the coils 16 of said helical length 8 extend around a longitudinal axis Y-Y which coincides with the axis X-X of the proximal portion 4 of the tubular body 3 of the capture member 2 (FIGS. 1, 5, 7, 9, and 36).

In accordance with an embodiment, a further preferably rectilinear distal length 22 is provided distally to said helical length 8, ending in said tip 7. Preferably, said rectilinear distal length 22 has a predefine length and is selected so as, for example, to make the device insertion less traumatic. For example, in the case of insertion of the device in tortuous zones, said distal length abuts against the wall of the duct or vessel allowing a soft movement and avoiding traumatizing or dissecting the vessel wall. Furthermore, said distal length can act as a guide, and allow the capture member to be centred relative to the vessel (FIGS. 1, 3, 5, 17, 19, 21, 34, 36).

Figures 7, 8:
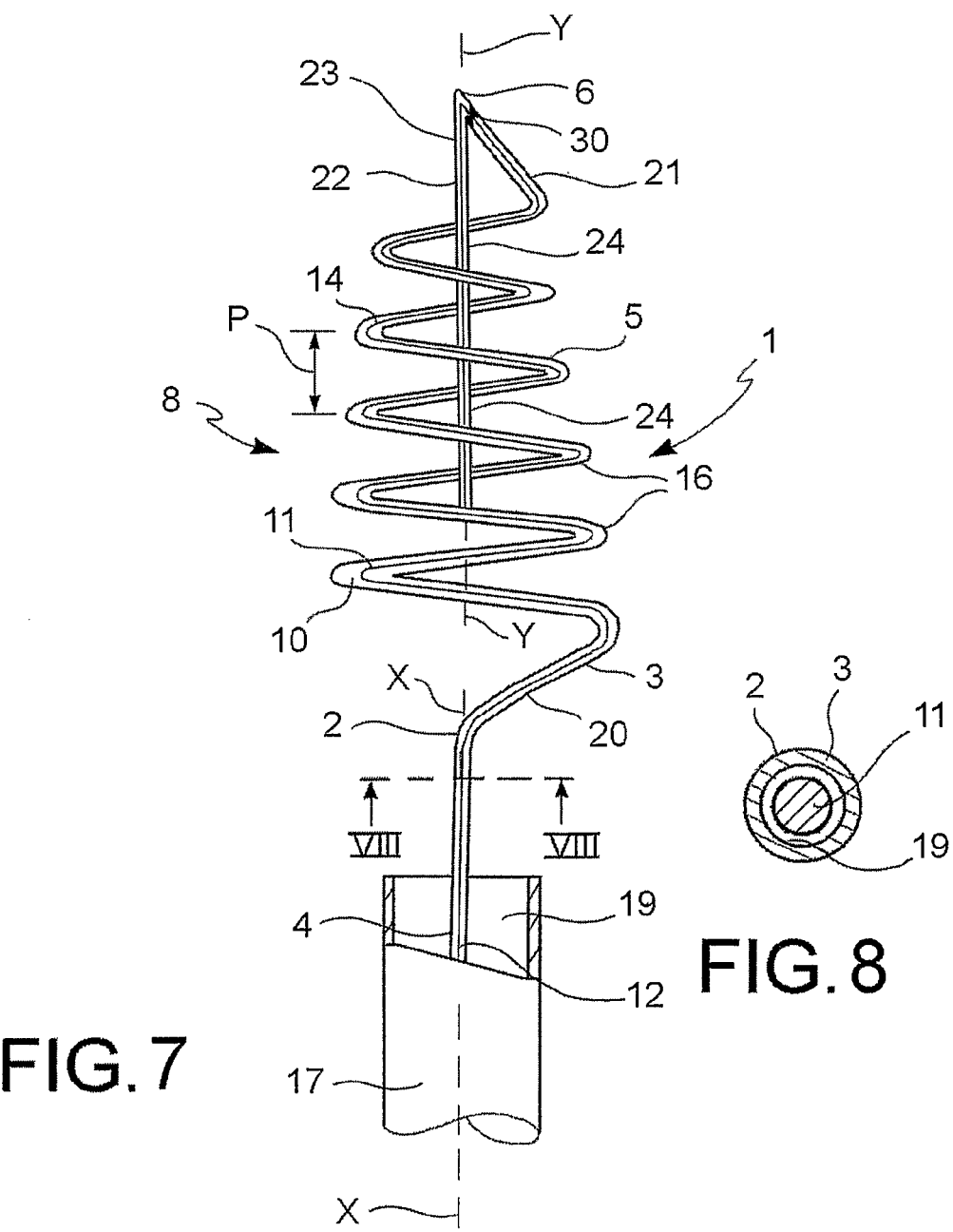
FIG. 7 illustrates, according to a still further embodiment, a sectional view of a micro-catheter distal end from which a capture member distally protrudes in a deployed and relaxed position, in which an inner cable is received.
FIG. 8 illustrates the section according to the line VIII-VIII of the capture member with cable of FIG. 7.
Figures 11, 12:
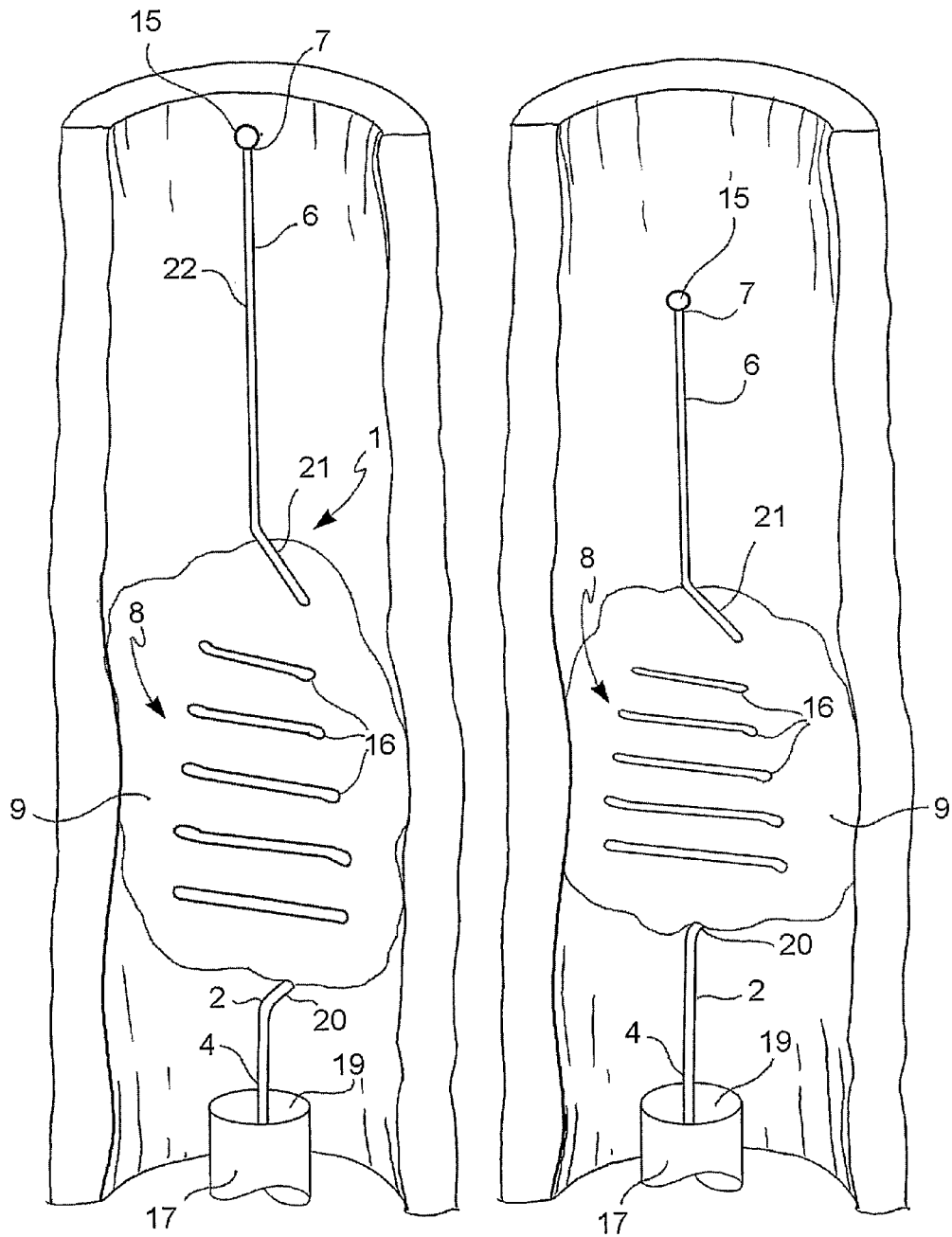
FIG. 11 illustrates an withdrawal step of a blood clot from a vessel with a device according to an embodiment.
FIG. 12 illustrates an withdrawal step of a blood clot from a vessel with a device according to a further embodiment.
Figure 15:
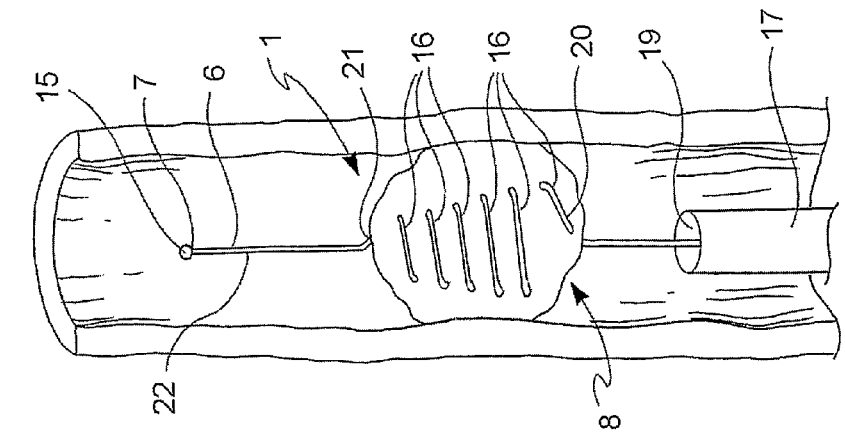
FIGS. 13, 14, and 15 show three further withdrawal steps of a blood clot from a vessel.
Figure 14:
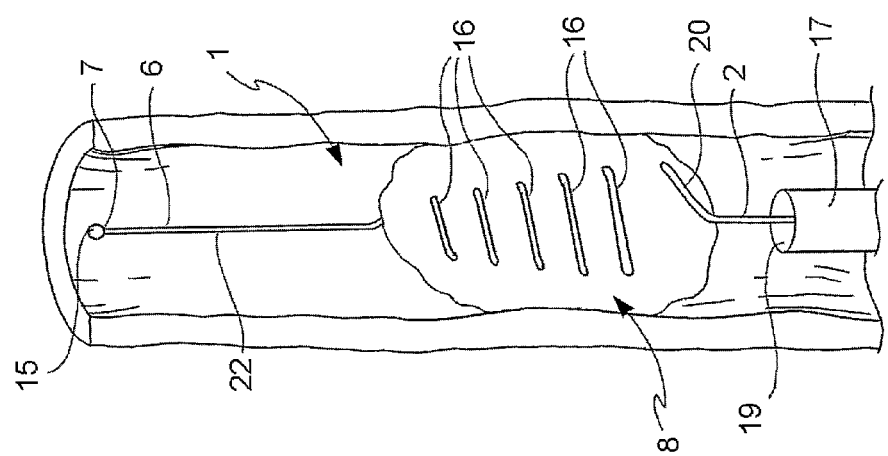
Figure 13:
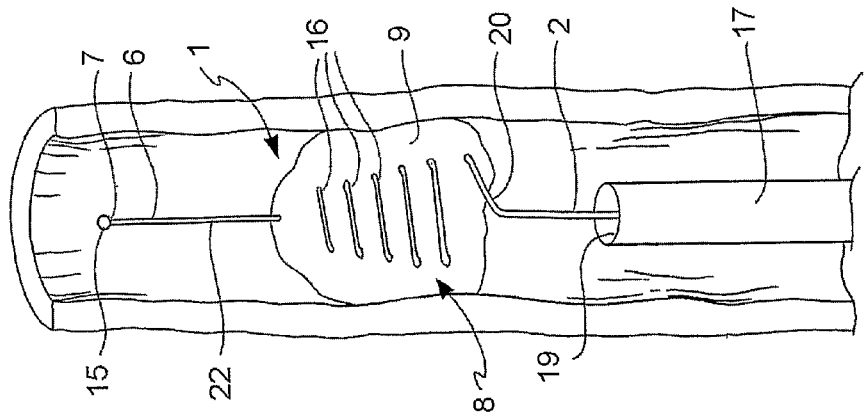
Figure 22:
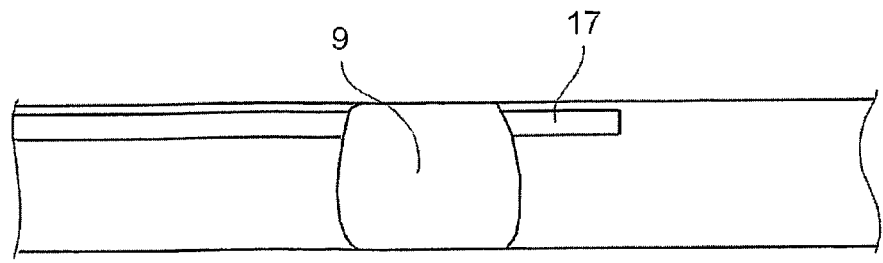
FIGS. 22 to 26 show in side view five deployment steps of the capture member downstream a blood clot.
Figure 23:
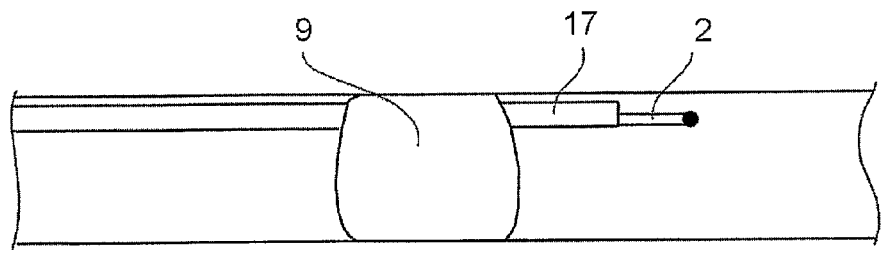
Figure 24:
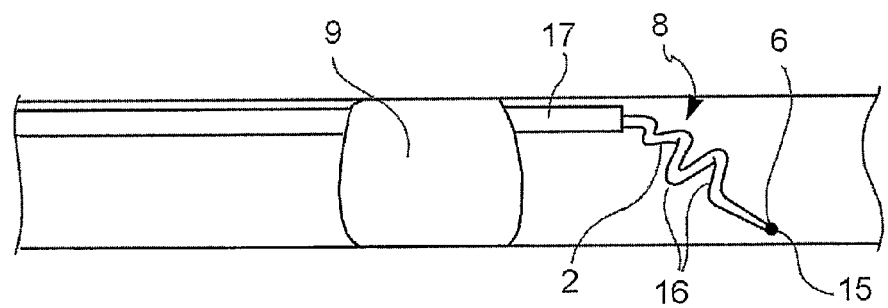
Figure 25:
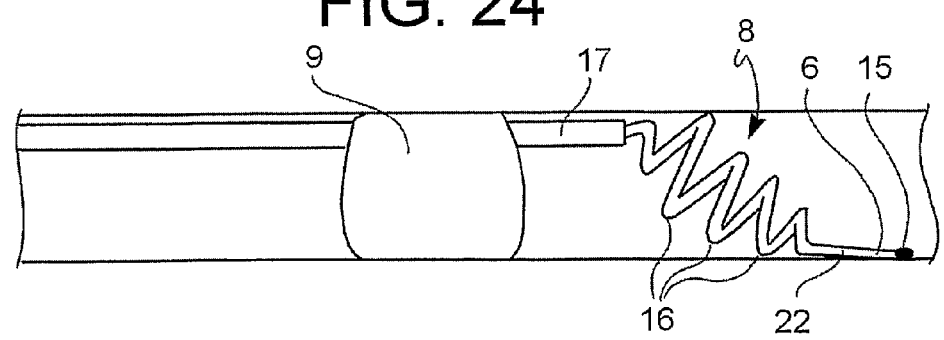
Figure 26:
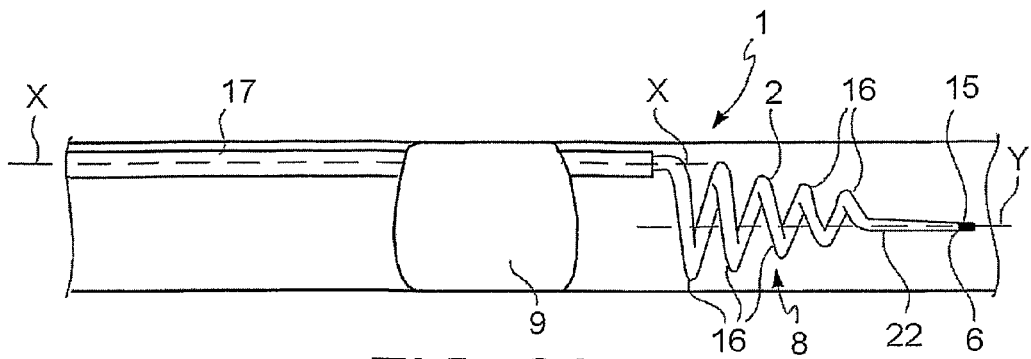
Figure 27:
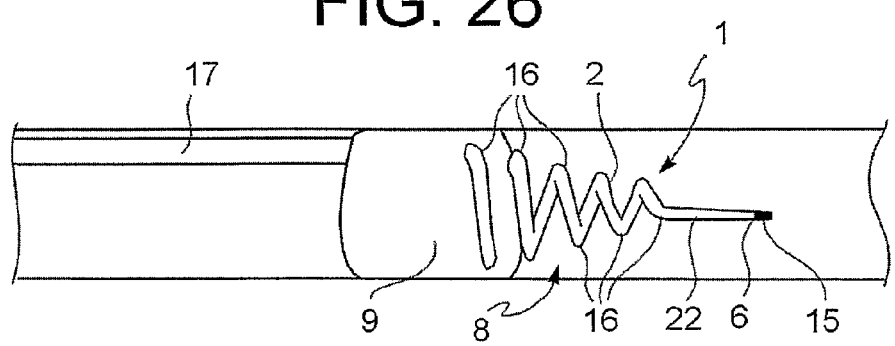
FIGS. 27 to 33 illustrate seven capture and removal steps of a blood clot from a vessel.
Figure 28:
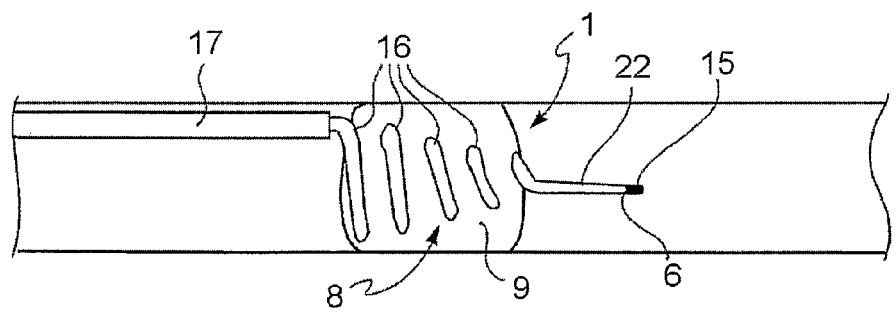
Figure 29:
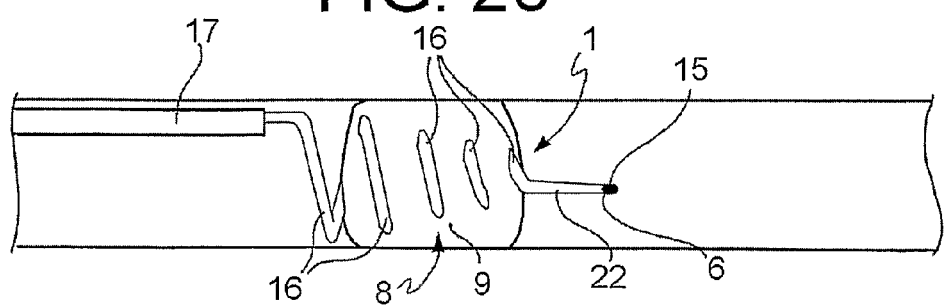
Figure 30:
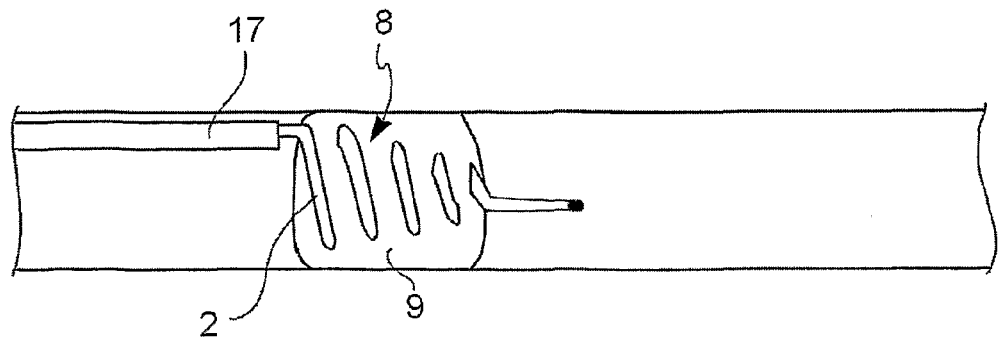

In accordance with an embodiment, said further distal length 22 comprises a folded portion 23 towards the tubular body 3 proximal portion 4, starting from the apical end 6, preferably entering with a length 24 of said folded portion 23 between said helical coils 16 of the helical length 8 where the blood clot 9 is received, so as, for example, to at least partially insert said length 24 of said folded portion 23 in the blood clot 9 and to secure it to the device 1 (FIGS. 7, 9, 36).

In accordance with an embodiment, a further preferably rectilinear first distal length 22 is provided distally to said helical length 8, ending in said tip 7, and at the same time a further folded portion 23 is provided towards the proximal portion 4 of the tubular body 3, preferably entering with a length 24 of said folded portion 23 between said helical coils 16 of the helical length 8 where the blood clot 9 is received (FIG. 36).

In accordance with an embodiment, said inner cable 11 is in an elastic material, for example, metallic or with shape memory, for example, Nitinol™. In accordance with an embodiment, said inner cable 11 is in polymeric elastic material.

In accordance with an embodiment, said inner cable 11 comprises a tip 15 having dimensions which are higher than the lumen 10 of the tubular body 3 of the blood clots 9 capture member 2, adapted to be secured to the tubular body 3 tip 7. For example, said cable 11 comprises a tip 15 which is essentially spherical or ogival-shaped (FIGS. 3, 21, and 37).

In accordance with an embodiment, the cable 15 tip is welded to the tubular body 3 tip 7.

In accordance with an embodiment, the cable 15 tip is secured by mechanical coupling to the tubular body 3, for example, by geometrical force fit.

In accordance with an embodiment, a securing portion 30 of the inner cable 11 is mechanically connected, for example, by interference shape fit, to the tubular body 3 apical end 6. For example, in the case the capture member 2 has a further distal length 22 comprising a folded portion 23 towards the tubular body 3 proximal portion 4, starting from the apical end 6, preferably entering with a length 24 of said folded portion 23 between said helical coils 16 of the helical length 8 where the blood clot 9 is received, the inner cable 11 is secured, for example, by deforming the capture member 2 tubular body 3 against the inner cable 11, for example, in a special annular seat provided in the inner cable 11, in the proximity of the capture member 2 apical end 6 which results to be more distal relative to the tip 7 folded between the coils 16.

In accordance with an embodiment, said inner cable 11 has a tubular cable body 32 defining a cable lumen 33.

In accordance with an embodiment, at the proximal maneuvering end 13 of the inner cable 11, indicating members 26 of the cable 11 position relative to the tubular body 3 are associated, directly or by means of maneuvering members 25, for example, chromatic indicating members or graduated indicating members capable of indicating the inner cable 11 relative position relative to the tubular body 3 (FIG. 34).

In accordance with an embodiment, the proximal end tubular body 3 has a maneuvering portion 31 comprising an adjustable coupling with maneuvering members 25 of the inner cable 11, so as to adjust the relative position of the inner cable 11 and the tubular body 3 proximal portions.

Advantageously, the capture member 2 tubular body 3 comprises a preferably externally threaded handle 34 at the proximal end 4, on which a closure member 35 is screwed, to which the inner cable 11 proximal end 12 is connected, for example, in accordance with an embodiment, received in a seat provided in the closure member 35 which allows an axial traction from the inner cable 11, thus avoiding a rotation or torsion thereof during the adjustment.

Thanks to the threaded coupling between handle 34 and closure member 35, it will be possible to precisely adjust the relative position between the proximal end 4 of the tubular body 3 and of the inner cable 11, by tensioning the inner cable 11 which results to be firmly secured to the tubular body 3 apical end 6 and to consequently precisely adjust the pitch "p" between the helical coils 16.

In accordance with a still different embodiment, said tip 15 of said inner cable 11 is secured to said apical end 6 of said tubular body 3 of the capture member 2 so that, when said inner cable 11 is subjected to a relative movement relative to the capture member 2 in the distal direction, said inner cable 11 moves the tubular body 3 the apical end 6 away from the proximal portion thereof, increasing the pitch "p" of said coils 16 of the helical length 8 of the blood clot 9 capture member 2, until advantageously bringing them to an essentially rectilinear configuration. For example, this embodiment, which results to be less flexible than those previously described, can be used where the path to be traveled by the device is less tortuous, but with very reduced dimensions, for example, with vessels having very small cross-sections, allowing reaching the blood clot and passing beyond it without using further containment members as a micro-catheter. Once the blood clot has been passed, the inner cable 11 is released by bringing the coils 16 back to a helical position, and the inner cable 11 is used during the capture and traction of the blood clot to adjust the strain of the helical length 8 and, particularly, the pitch "p" between the coils 16.

In accordance with a preferred embodiment, a micro-catheter 17 is comprised, having tubular body 18 defining a micro-catheter lumen 19 with predefined transversal dimensions and adapted to receive said capture member 2 which, when completely received into said micro-catheter 17, is urged by the inner walls of the micro-catheter tubular body to unfold the helical length 8, thus bringing it to an essentially rectilinear configuration. In this case, the capture member 2 is received in the micro-catheter 17 in a non-stressed condition, therefore it results to be particularly flexible and adapted to the handling thereof in a particularly tortuous path.

In accordance with an embodiment, a proximal catheter or catheter 27 is comprised, with tubular body 28 comprising a lumen 29 adapted to receive the micro-catheter 17, with the capture member 2 having the distal portion thereof with the helical length 8 arranged with the coils thereof 16 in a helical or deployed position for the capture of a blood clot 9. Thanks to the catheter 27, it is possible to retract the capture member 2 with the anchored blood clot 9 within the catheter lumen 29 and to remove the blood clot from the vessel.

Said catheter 27 is, for example, useful also to remove from the treated vessel optional small portions 36 of blood clot 36 which were to be split from the blood clot 9 main mass during the capture and removal manoeuvres, for example, by returning or sucking into the catheter lumen 29 a part of the fluid present in the vessel within the catheter after that the capture member 2 with the blood clot 9 have been completely retracted in the catheter lumen 29 (FIGS. 30 to 33).

Herein below a device assembling method according to the invention is set forth.

An assembling method of a blood clot removal device 1, comprising the steps of:

providing a device according to any one of the previously described embodiments;

inserting the inner cable 11 into the lumen 10 of the tubular body 3 of the capture member 2, through the tip 7 of the latter, starting from the proximal length thereof 12 until bringing the inner cable 11 tip 15 against the tubular body 3 tip 7;

firmly securing a securing portion 30 of the inner cable 11 to the tubular body 3 apical end 6, so that, when said inner cable 11 is subjected to a relative movement relative to the capture member 2 in the proximal direction, said inner cable 11 brings the tubular body 3 apical end 6 closer to the proximal portion 4 thereof, shortening the pitch "p" of said coils 16 of the helical length 8 of the blood clot 9 capture member 2 (FIGS. 16 to 19).

In accordance with an embodiment, the further step of making a portion of the inner cable 11 proximal length 12 to protrude from the tubular body 3 proximal end is provided.

In accordance with an embodiment, the further step of connecting a portion of the inner cable 11 proximal length 12 to the tubular body 3 proximal end by means 25, 31 allowing an adjustable relative movement is provided.

In accordance with an embodiment, the capture member 2 with the introduced inner cable 11 is introduced into a micro-catheter 17 (FIGS. 20 and 21).

Figure 31:
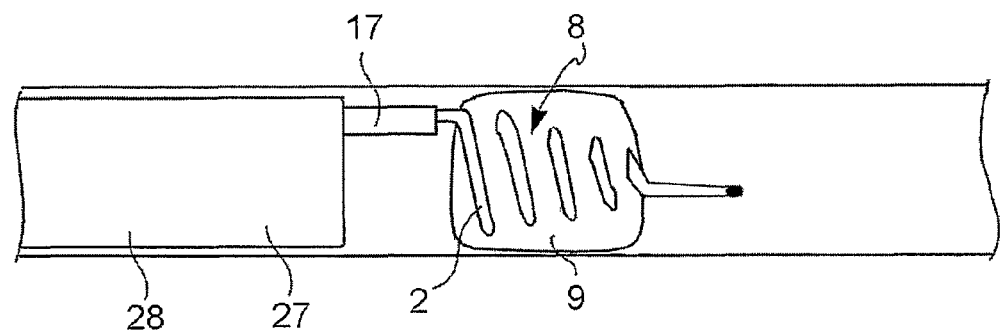
Figure 32:
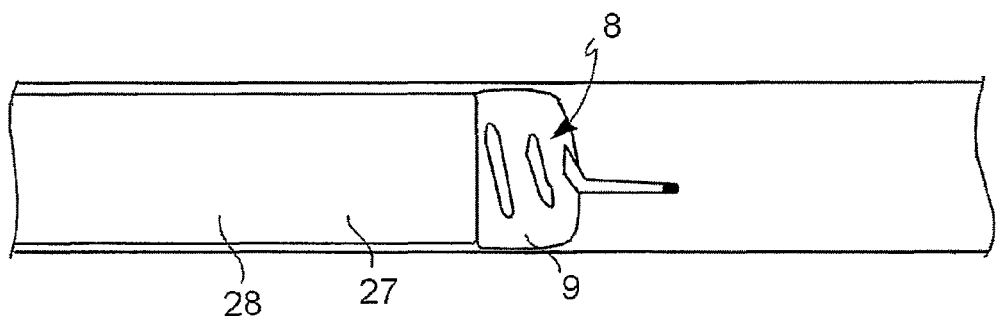
Figure 33:
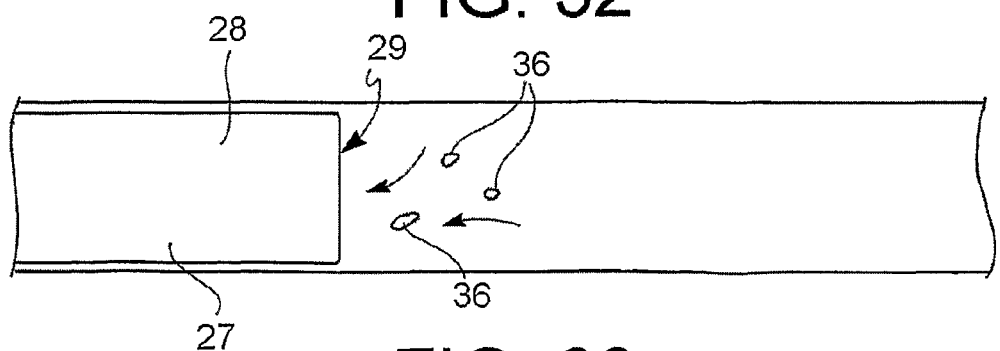

In accordance with an embodiment, the capture member 2 with the introduced inner cable 11 is introduced, with or without a micro-catheter 17, in a proximal catheter or catheter 27 (FIGS. 31 and 32).

Herein below, possible use methods of the device which is the object of the invention are set forth.

A capture method of an object, not necessarily a blood clot in a vessel or anatomic duct, comprising the steps of:

providing a blood clot removal device 1 according to any one of the above-described embodiments;

arranging the entire capture member 2 helical length 8 distally to the object to be captured, leaving part of the tubular body 3 proximal portion 4 proximally to the object to be captured, and with the proximal end thereof accessible for the handling thereof;

proximally returning the capture member 2, making so that the object to be captured is at least partially received in the helical length 8;

when the helical length 8, upon capturing and dragging the object to be captured, elastically strains, thus increasing the pitch "p" of the coils 16 thereof, proximally returning the inner cable 11, so as to bring the tubular body 3 apical end 6 closer to the proximal portion 4 thereof, shortening the pitch "p" of said coils 16 of the helical length 8 of the capture member 2 (FIGS. 22 to 33).

In accordance with an embodiment, there are provided the further steps of:

before arranging the helical length 8 distally to the object to be captured, passing through or beyond the object to be captured, arranging the tubular body 3 helical length 8 in an essentially rectilinear position;

once the object to be captured has been passed beyond at least with the helical length 8, deploying the coils 16 so that they take an helical shape distally to the object to be captured.

In accordance with an embodiment, the tubular body 3 of the capture member 2 is brought in an essentially rectilinear position by introducing it, with also the thereof helical length 8, into a micro-catheter 17 with a micro-catheter lumen 19 with predefined transversal dimensions and adapted to receive said capture member 2 which, when completely received in said micro-catheter 17, is urged, and deploys the helical length 8, bringing it to an essentially rectilinear configuration.

In accordance with an embodiment, the capture member 2 tubular body 3 is brought to an essentially rectilinear position by pushing an inner cable 11, the distal length 14 of which is firmly secured to the tubular body 3 apical end 6, in the tubular body 3 lumen 10 and mutually longitudinally spacing apart the helical length 8 coils 16.

The solution will be able to take, in the practice implementation thereof, also shapes and configurations different from those illustrated above, without for this anyhow departing from the present protection scope. Furthermore, all the details will be able to be replaced with technically equivalent elements, and the shapes, dimensions, and materials employed will be able to be any, according to the needs.

The invention claimed is:

1. A blood clot removal device, comprising:
a capture member having tubular body of prevailing longitudinal extension and provided with a lumen longitudinally extending in said tubular body, said tubular body having at least one proximal portion, at least one distal portion, an apical end of said distal portion, and a tip;
said at least one distal portion of said capture member having at least one helical length provided with coils wrapped in an helical manner forming a pitch (p) one relative to the other in the longitudinal direction, wherein the at least one distal portion of said capture member takes the at least one helical length when in a relaxed condition;
an inner cable received in said longitudinal lumen of said tubular body so as to extend through an entirety of said helical length of the tubular body, said inner cable comprising a proximal length having a proximal manoeuvring end and a distal length provided with a tip;
wherein at least one securing portion of said distal length of said inner cable is secured to said apical end of said tubular body of the capture member, said securing portion being firmly secured to said apical end so that, when said inner cable is subjected to a relative movement relative to the capture member in the proximal direction, said inner cable brings the apical end of the tubular body closer to the proximal portion thereof shortening the pitch (p) of said coils of the helical length of the capture member.

2. The device according to claim 1, wherein said securing portion of said inner cable is the cable tip, and said apical end of the tubular body is the tubular body tip.

3. The device according to claim 1 or 2, wherein said capture member, at least in the helical length thereof, is in a shape memory elastic material adapted to remain elastic also when stressed in an essentially rectilinear deployed configuration.

4. The blood clot removal device according to claim 1 or 2, wherein at least one proximal length of the capture member is in a first material adapted to support at least stresses adapted to retract said capture member to remove a blood clot, and at least one helical length of the capture member in a shape memory elastic material adapted to remain elastic also when stressed in an essentially rectilinear deployed configuration.

5. The device according to any one of the claims 1 to 2, wherein said helical length extends along a longitudinal axis (Y-Y) from a proximal end to a distal end, and comprises a plurality of coils which little by little approach said longitudinal axis (Y-Y) passing from said proximal end to said distal end, so as to constitute a receptacle or pocket transversally arranged to a vessel and forming a seat able to capture, at least partially contain, and retain, a blood clot to be removed.

6. The device according to claim 5, wherein said helical length has a dimension with a conical or frusto-conical shape.

7. The device according to any one of the claims 1 to 2, wherein said coils of said helical length have essentially a helical shape of a diameter decreasing from 5 mm at the proximal end of the helical length to a diameter of 1 mm at the distal end of the helical length.

8. The device according to any one of the claims 1 to 2, wherein said helical length has from 3 to 9 coils.

9. The device according to any one of the claims 1 to 2, wherein the coils of said helical length are arranged eccentrically relative to the proximal portion of the tubular body of the capture member so as to let that said helical length freely act to capture a blood clot.

10. The device according to any one of the claims 1 to 2, wherein a rectilinear further distal length ending in said tip is provided distally to said helical length.

11. The device according to claim 10, wherein said further distal length comprises a folded portion towards the proximal portion of the tubular body starting from the apical end, preferably entering with a length of said folded portion between said helical coils of the helical length where the blood clot is received so as to at least partially insert said length of said folded portion in the blood clot and secure it to the device.

12. The device according to any one of the claims 1 to 2, wherein said inner cable is in an elastic material.

13. The device according to any one of the claims 1 to 2, wherein the tip of said inner cable comprises dimensions which are greater than those of the lumen of the tubular body of the capture member, and wherein the tip is adapted to be secured to the tubular body tip.

14. The device according to any one of the claims 1 to 2, wherein the inner cable tip is welded to the tubular body tip.

15. The device according to any one of the claims 1 to 2, wherein a securing portion of the inner cable is mechanically connected by interference fit to the tubular body apical end.

16. The device according to any one of the claims 1 to 2, wherein said inner cable has a tubular cable body defining a cable lumen.

17. The device according to any one of the claims 1 to 2, wherein the inner cable proximal manoeuvring end comprises indicating members configured to indicate the position of the cable relative to the tubular body.

18. The device according to any one of the claims 1 to 2, wherein the tubular body proximal end has a manoeuvring portion comprising an adjustable coupling with manoeuvring members configured to adjust the relative position of the proximal length of the inner cable and the proximal portion of the tubular body.

19. The device according to any one of the claims 1 to 2, wherein the device further comprises a micro-catheter having a tubular body defining a micro-catheter lumen of predefined transversal dimensions and adapted to receive said capture member which, when completely received in said micro-catheter lumen, unfolds the helical length bringing it to an essentially rectilinear configuration.

20. The device according to claim 19, wherein the device further comprises a catheter with tubular body comprising a lumen adapted to receive the micro-catheter with the capture member having the distal portion thereof with the helical length arranged with the coils thereof in a helical or deployed position for the capture of a blood clot.

21. The blood clot removal device according to any one of the claims 1 to 2, wherein said tip of said inner cable is secured to said apical end of said tubular body of the capture member so that, when said inner cable is subjected to a relative movement relative to the capture member in the distal direction, said inner cable moves the tubular body apical end away from the proximal portion thereof, increasing the pitch (p) of said coils of the helical length of the capture member.

22. An assembling method of a blood clot removal device, comprising the steps of:
    providing a device according to any one of the claims 1 to 2,
    inserting the inner cable in the lumen of the tubular body of the capture member, through the tip of the latter, starting from the proximal length thereof until brining the tip of the inner cable to the tubular body tip,
    firmly securing a securing portion of the inner cable to the tubular body apical end, so that, when said inner cable is subjected to a relative movement relative to the capture member in the proximal direction, said inner cable brings the tubular body apical end closer to the proximal portion thereof, shortening the pitch (p) of said coils of the helical length of the blood clot capture member.

23. The assembling method according to claim 22, wherein the further step of making a portion of the inner cable proximal length to protrude from the tubular body (3) proximal end is provided.

24. The assembling method according to claim 22, wherein the further step of connecting a portion of the inner cable proximal length from the tubular body proximal end by means for allowing an adjustable relative movement is provided.

25. The assembling method according to claim 22, wherein the capture member with the inner cable is introduced in a micro-catheter.

26. The assembling method according to claim 22, wherein the capture member with the inner cable is introduced, with or without a micro-catheter, in a catheter.

27. A non-therapeutic and non-surgical method for the capture of an object, comprising the steps of:
    providing a blood clot removal device according to any one of the claims 1 to 2;
    arranging the capture member helical length distally to the object to be captured, leaving part of the tubular body proximal portion proximally to the object to be captured and with the proximal end thereof accessible for the handling thereof;

proximally returning the capture member, making so that the object to be captured is at least partially received in the helical length;

when the helical length, upon capturing and dragging the object to be captured elastically strains, increasing the pitch (p) of the coils, proximally returning the inner cable by moving the manoeuvring end thereof away from the tubular body proximal portion, so as to bring the tubular body apical end closer to the proximal portion thereof, shortening the pitch (p) of said coils of the capture member helical length.

28. The method according to claim 27, wherein there are provided the further steps of:

before arranging the helical length distally to the object to be captured, passing the object to be captured through or beyond by arranging the tubular body helical length in an essentially rectilinear position;

once the object to be captured has been passed beyond at least with the helical length, deploying the coils so that they take a helical shape distally to the object to be captured.

29. The method according to claim 27, wherein the capture member tubular body is brought to an essentially rectilinear position by introducing it with also the helical length thereof in a micro-catheter with a micro-catheter lumen of predefined transversal dimensions and adapted to receive said capture member which, when completely received in said micro-catheter, unfolds the helical length thus bringing it in an essentially rectilinear configuration.

30. The method according to claim 27, wherein the capture member tubular body is brought to an essentially rectilinear position by pushing the inner cable, the distal length of which is firmly secured to the tubular body apical end, in the tubular body lumen, and longitudinally moving the helical length coils away one from the other.

* * * * *